United States Patent [19]

Fattore et al.

[11] 4,082,785

[45] Apr. 4, 1978

[54] MANUFACTURE OF ACRYLONITRILE FROM PROPYLENE, AMMONIA AND OXYGEN

[75] Inventors: Vittorio Fattore; Bruno Notari, both of San Donato Milanese, Italy

[73] Assignee: Snamprogetti, S.p.A., Milan, Italy

[21] Appl. No.: 220,712

[22] Filed: Jan. 25, 1972

[30] Foreign Application Priority Data

Jan. 25, 1971 Italy .................. 19723 A/71

[51] Int. Cl.$^2$ .......................................... C07C 120/14
[52] U.S. Cl. ................. 260/465.3; 252/437; 252/439; 260/604 R
[58] Field of Search ........................ 260/465.3

[56] References Cited

U.S. PATENT DOCUMENTS

| 3,161,671 | 12/1964 | Minerawa et al. | 260/465.3 |
|---|---|---|---|
| 3,164,626 | 1/1965 | Minekawa et al. | 260/465.3 |
| 3,164,627 | 1/1965 | Minekawa et al. | 260/465.3 |
| 3,164,628 | 1/1965 | Minekawa et al. | 260/465.3 |
| 3,338,952 | 8/1967 | Callahan et al. | 260/465.3 |
| 3,412,135 | 11/1968 | Eden | 260/465.3 |
| 3,471,545 | 10/1969 | Giordano et al. | 260/465.3 |
| 3,542,842 | 11/1970 | Grasselli et al. | 260/465.3 |
| 3,551,470 | 12/1970 | Shaw et al. | 260/465.3 |
| 3,625,867 | 12/1971 | Yoshino et al. | 260/465.3 X |
| 3,641,102 | 2/1972 | Reulet et al. | 260/465.3 |

*Primary Examiner*—Joseph Paul Brust
*Attorney, Agent, or Firm*—Morgan, Finnegan, Pine, Foley & Lee

[57] ABSTRACT

A new catalyst is described which is useful in the ammoxidation or oxidation of olefins. It consists of a mixture of oxidation compounds of uranium, tellurium and molybdenum, which may be accompanied by an activator consisting of an oxidation compound of an element selected from groups Ib, IIa, IIb, IIIa, IIIb, IVa, Va, VIb, VIIb and VIII of the periodic system, and is represented by the formula: $U_a Te_b Mo_c Me_d X$ wherein, U is uranium, Te is tellurium, Mo is molybdenum, Me is the activator element, X is the oxygen necessary for saturating the other valences, $a$ is 1, $b$ is 1 to 8, $c$ is 0.1 to 1 and $d$ is 0 to 5. In the use of that catalyst, unsaturated nitriles are prepared by contacting a mixture, in vapor phase, of an olefin, ammonia and oxygen or a gas containing oxygen in the presence of the catalyst; and olefins are converted to oxygen containing compounds or dienes by contacting, in vapor phase, a mixture of the olefin and oxygen in the presence of the catalyst.

4 Claims, No Drawings

MANUFACTURE OF ACRYLONITRILE FROM PROPYLENE, AMMONIA AND OXYGEN

The present invention relates to a catalyst composition and to its applications to the manufacture of unsaturated nitriles and to the oxidation of olefines to oxygenated compounds or dienes.

For simplicity sake, but unrestrictively, in the continuation of the description reference will be made to the case in which the olefine is propylene, the unsaturated nitrile is acrylonitrile and the oxygenated compound is acrolein.

In the art different catalyst compositions are known for the production of unsaturated nitriles starting from ammonia, propylene and oxygen or gases containing oxygen or for the oxidation of olefines with oxygen or gases containing oxygen.

Among them we can quote the heteropolysalts obtained by heteropolyacids salified with tellurium or bismuth, wherein the co-ordinative radical having an acid character is selected either among the rare earth elements of the lanthanum series as lanthanum or cerium or among the elements of the actinium series as thorium; the co-ordinative radical is co-ordinated with the elements tungsten and/or molybdenum. Said heteropolycompounds have a well defined chemical formula wherein the ratios among the various atoms constituting the molecule is well fixed.

The above defined compounds and the other catalyst compositions known in the art do not give completely satisfactory results when used for the olefines ammoxidation or for the oxidation of the same, particularly with reference to the propylene conversion, to the selectivity to acrylonitrile or to acrolein and consequently with regard to the yields.

An object of the present invention is a catalyst composition based on oxygen containing compounds of uranium, tellurium, molybdenum with or without at least an oxygen containing compound of an element of the groups Ib, IIa, IIb, IIIa, IIIb, IVa, Va, Vb, VIb, VIIb, VIII of the periodic table (Handbook of Chemistry and physics — 39th Edition 1957–1958; pages 400–401; Chemical Rubber Publishing Co.); said catalyst mixture is suitable for the manufacture of acrylonitrile from propylene, ammonia and oxygen or gas containing oxygen according to the reaction:

$$C_3H_6 + NH_3 + 1.5O_2 = C_3H_3N + 3H_2O$$

or for the manufacture of acrolein starting from propylene and oxygen or gas containing oxygen according to the reaction:

$$C_3H_6 + O_2 = C_3H_4O + H_2O$$

obtaining for both reactions very high conversions of propylene and high selectivities to acrylonitrile or to acrolein. It has been in fact surprisingly found that a mixture composed of an oxygen containing compound of tellurium, of an oxygen containing compound or uranium, of an oxygen containing compound of molybdenum with or without at least an activator constituted by an oxygen containing compound of an element of the groups Ib, IIa, IIb, IIIa, IIIb, IVa, Va, Vb, VIb, VIIb, VIII of the periodic system, in particular phosphorus, arsenic, antimony and boron furnishes a catalyst capable of giving high conversions of propylene and a high selectivity to acrylonitrile and to acrolein.

The above mentioned oxygen containing compounds particularly but unrestrictively are in the form of oxides, even though some of them can be combined so as to form a compound containing oxygen in its molecule; one of said compounds is in particular $(UO_2)TeO_3$.

It is important to observe with attention that the catalytic mixture object of the present invention does not correspond to the chemical formula of a single particular compound, because the ratios among the various elements constituting the same will differ from the stoichiometric ratio of a well defined oxycompound.

For said reason when there is the presence in the catalytic mixture of a compound containing a combination of some of the above mentioned elements, contemporaneously there will be always present other oxygen containing compound, in particular other oxides in order to have the desired ratio among the various elements constituting the mixture. The catalytic mixture object of the present invention can be represented by the following formula:

$$U_a Te_b Mo_c Me_d X$$

wherein U is uranium, Te is tellurium, Mo is molybdenum, Me is an activator selected among the elements of the groups Ib, IIa, IIb, IIIa, IIIb, IVa, Va, Vb, VIb, VIIb, and VIII of the periodic system, preferably phosphorus, arsenic, antimony or boron; X is oxygen in such an amount to saturate the valence of the aforesaid elements: in said formula for $a$ equal to 1, $b$ is in the range of from 1 to 8, preferably from 2 to 5, $c$ is in the range of from 0.1 to 1, preferably from 0.3 to 0.8, $d$ is in the range of from 0 to 5 and preferably from 0 to 3.

The catalytic mixtures object of the present invention can be used as such or supported on titanium oxides, silica and other conventional substances suitable for use as carriers; among said carriers the preferred one is titanium oxide and the percentages by weight of the carrier in the supported catalysts object of the invention range from 0.5% to 95%. The catalysts object of the present invention can be prepared starting from salts, acids, oxides of the various constituting elements and in the case of tellurium also from the same metal according to procedures well known in the art as, for instance, coprecipitation, atomization, impregnation and the like.

In a preferred procedure, for a catalyst to be used in a fixed bed, we prepared an aqueous solution of uranyl nitrate and an aqueous solution of ammonium molybdate and of telluric acid; the two solutions were mixed by pouring the first one into the second and subsequently brought to dryness under continuous stirring.

The obtained mass was treated according to conventional techniques as extrusion, tabletting, granulation for confering to the same the size and the form desired in the utilization.

The catalyst was at last calcined at temperatures in the range of from 450° C to 550° C for 4 hours.

A further object of the present invention is the process for the manufacture of an unsaturated nitrile starting from an olefin, ammonia and oxygen or gas containing oxygen, use being made of the above mentioned catalyst.

We will refer now to the case in which the olefin is propylene, the unsaturated nitrile is acrylonitrile, even though the process is applicable to the manufacture of any other unsaturated nitrile.

The vapour phase mixture of propylene, ammonia and oxygen or gas containing oxygen with an ammonia/propylene molar ratio in the range of from 0.05/1 to 5/1 and preferably from 0.7/1 to 1.5/1 and an oxygen/propylene ratio in the range of from 0.5/1 to 3/1, preferably from 1/1 to 2/1, is fed, preferably in presence of steam, to a reactor having a catalyst fixed or fluidized bed wherein the temperature is maintained between 300° C and 550° C, preferably between 350° C and 490° C and the pressure is the atmospheric one or slightly higher than the atmospheric one.

The contact time is in the range of from 0.1 to 50 sec, preferably from 1 to 15 sec. For contact time we mean the ratio between the volume of the catalytic mass and the volume of the reactant gases fed to the reactor for unit of time, the time being expressed in seconds and the volume in cubic centimeters, the gas being considered at the conditions of room temperature and of atmospheric pressure. The conversions and the selectivities with the precedingly described process are, as said, industrially interesting.

A further object of the present invention is the manufacture of oxygen containing compounds starting from olefines and oxygen.

We will refer particularly to the case in which the olefine is propylene and the oxygen containing compound is acrolein.

The vapour phase mixture of propylene and oxygen or gas containing oxygen is fed, in presence of steam, to a reactor having a catalyst fixed or fluidized bed wherein the temperature is maintained between 350° C and 550° C, preferably between 390° C and 480° C, and the pressure is the atmospheric one or slightly higher than the atmospheric one.

The contact time is in the range of from 0.1 to 50 sec and preferably from 1 to 15 sec. It is clearly visible from the following examples that the catalytic mixture object of the invention brings industrially interesting results both in the case of the ammoxidation of olefins and in the oxidation of the same.

Some unrestrictive examples will now be given for better illustrating the invention. In said examples for propylene conversion, selectivity to acrylonitrile (ACN) and yields we mean the data obtained by means of the following formulae:

$$C_3H_6 \text{ conversion } \% = \frac{\text{moles of } C_3H_6 \text{ entering the reactor } - \text{ moles of } C_3H_6 \text{ leaving the reactor}}{\text{moles } C_3H_6 \text{ entering the reactor}} \times 100$$

$$\text{selectivity to ACN } \% = \frac{\text{moles of produced acrylonitrile}}{\text{moles of } C_3H_6 \text{ entering the reactor } - \text{ moles of } C_3H_6 \text{ leaving the reactor}} \times 100$$

$$\text{acrylonitrile yield } \% = \frac{\text{moles of produced acrylonitrile}}{\text{moles of } C_3H_6 \text{ entering the reactor}} \times 100$$

EXAMPLE 1

12 grams of hexahydrate uranyl nitrate were dissolved in 100 cc of distilled water. Separately a solution of ammonium molybdate and telluric acid was prepared by dissolving in 100 cc of water 51 g of $(NH_4)_6Mo_7O_{24}\cdot 4H_2O$ and 18.6g of $H_2TeO_4$.

The two solutions were mixed pouring the first into the second one. They were dried by heating on an electric hot plate under continuous stirring.

The residue was calcined at 530° C for 4 hours in a muffle. The catalytic composition by moles was: $UO_3.4\ TeO_2.12\ MoO_3$.

The catalytic mass was ground and a portion of 6 cc. having a granulometry in the range of from 50 to 100 mesh ASTM was tested in a microreactor into which propylene, ammonia, air and steam were fed in a volume ratio 1/1.3/12/10. The reaction products analysis was carried out on the effluent stream from the reactor by gas-chromatography.

At 450° C. with a contact time of 6 sec we had a molar conversion of propylene of 12% and a selectivity to acrylonitrile of 57%, and to acrolein of 7.2%. This example shows the low activity and selectivity to acrylonitrile of catalysts wherein molybdenum is present with respect to the other elements in such ratios that essentially heteropolymolybdates are formed.

EXAMPLE 2

According to the procedure of example 1 a catalyst was prepared wherein the atomic ratios of the elements constituting the active part were: Te/U/Mo = 8 : 2 : 1.

For said purpose we used 50 g of $UO_2(NO_3)_2\cdot 6H_2O$, 78 g of $H_2TeO_4$, 9 g of $(NH_4)_6Mo_7O_{24}\cdot 4H_2O$ and 400 cubic centimeters of distilled water.

The catalyst at 460° C with a contact time of 11 seconds and a ratio of the feed reactants $C_3H_6/NH_3/\text{air}/H_2O$ equal to 1/1.2/12/10 gave the following results:
propylene conversion: 80.7%
selectivity to acrylonitrile: 83%
selectivity to acetonitrile: 1.7%
selectivity to acrolein: 2.2%

EXAMPLE 3

A catalyst having the same composition as the one of example 2 was supported on titanium oxide. Titanium oxide was added to the solution of the active part before the drying in such an amount that in the catalyst 50% of carrier was present.

The catalyst was calcined at 530° C for 4 hours and 6 cc were tested in a microreactor.

At 470° C with a ratio in the feed among $C_3H_6/NH_3/\text{air}/H_2O$ equal to 1/1.1/12.5/15 and a contact time of 6 seconds we obtained the following results:
propylene conversion: 92.2%
selectivity to acrylonitrile: 78.5%
selectivity to acetonitrile: 3.1%
selectivity to acrolein: 0.9%

EXAMPLES 4 AND 5

A catalyst having the same composition as the one of example 2 was supported on silica.

In practice, we added 5000 g of a silica sol of the type "Ludox A.S." at 30% of $SiO_2$ (Du Pont), to such an amount of solution of the active elements that, after drying 3500 grams of active part were present.

The drying was carried out by atomization of the resulting solution. A calcination at 520° C for 8 hours was then effected.

The catalyst contained 70% of active part and 30% of silica.

The catalyst was tested in a microreactor in amount of 6 cc and in fluidized bed in a tube having an internal diameter of 38 mm, in which tube there were 200 cc of catalyst.

The working conditions and the results obtained in the fixed bed microreactor, example No. 4, and in the fluidized bed reactor, example No. 5, are reported on table 1.

TABLE 1

| Example | No. 4 | No. 5 |
|---|---|---|
| Reaction temperature | 470° C | 470° C |
| Contact time | 12 sec | 12 sec |
| Feed: $C_3H_6$ | 4.1% | 5.9% |
| $NH_3$ | 5.3% | 6.4% |
| Air | 49.6% | 70% |
| $H_2O$ | 41% | 17.7% |
| $C_3H_6$ conversion | 68% | 75% |
| Selectivity to acrylonitrile | 77% | 77% |

EXAMPLE 6 AND 7

100 g of $UO_2(NO_3)_2 \cdot 6H_2O$ were dissolved in 200 cc of distilled water. Separately a solution containing 18 g of $(NH_4)_6Mo_7O_{24} \cdot 4H_2O$ and 78 g of $H_2TeO_4$ was prepared.

The second solution was added to the first one and the resulting solution was dried on an electric hot plate under stirring.

The calcination was carried out at 500° C for 12 hours in a muffle. The atomic ratios among the components of the catalytic mass were U/Te/Mo = 1/2/0.5.

The catalyst was tested for the reaction of ammoxidation to acrylonitrile, example No. 6, and for the reaction of oxidation to acrolein, example No. 7, in the experimental conditions quoted together with the results in Table 2.

TABLE 2

| Example | No.6 | No. 7 |
|---|---|---|
| Reaction temperature | 450° C | 430° C |
| Contact time | 12 sec | 6 sec |
| Feed : $C_3H_6$ | 3.4% | 5.6% |
| $NH_3$ | 4.4% | — |
| Air | 41% | 67% |
| $H_2O$ | 51.2% | 27.4% |
| $C_3H_6$ conversion | 83% | 78% |
| Selectivity to acrylonitrile | 78.9% | — |
| Selectivity to acrolein | 1.6% | 80.1% |

EXAMPLE 8

50 g of uranyl nitrate were dissolved in 100 cc of water and 90 g of $H_2TeO_4 \cdot 2H_2O$ were dissolved in 200 cc of water. Separately 6 g of $(NH_4)HB_4O_7 \cdot 3H_2O$ were dissolved in 30 cc of water and 9 g of $(NH_4)_6Mo_7O_{24} \cdot 4H_2O$ were dissolved in another 30 cc of water. The four solutions were mixed and the resulting slurry was poured on 150 g of $TiO_2$.

The solution was dried under continuous stirring and the mass was calcined at 500° C for 4 hours.

At 460° C, with a feed ratio $C_3H_6/NH_3/Air/H_2O$ equal to 1/1.2/12/15 and a contact time of 6 seconds the following results were obtained:
propylene conversion: 92.3%
selectivity to acrylonitrile: 76.8%
selectivity to acrolein: 3.7%

EXAMPLE 9

A catalyst was prepared as in example 8, but, instead of the boron salt, 13 g of arsenic anhydride were utilized. At 465° C with a molar feed ratio $C_3H_6/NH_3/Air/H_2O$ equal to 1/1.2/12/15 and a contact time of 6 seconds, the following results were obtained.
propylene conversion: 92.8%
selectivity to acrylonitrile: 71.1%

EXAMPLE 10

A catalyst was prepared according to the description of example 8, but, instead of the boron salt, 8 g of antimony oxide in 30 cc of concentrated nitric acid were used.

At 465° C, with a molar feed ratio $C_3H_6/NH_3/Air/H_2O$ equal to 1/1.1/12/12 and a contact time of 6 seconds, the following results were obtained:
propylene conversion: 63.4%
selectivity to acrylonitrile: 83.7%

What we claim is:

1. A process for the manufacture of acrylonitrile characterized in that a mixture of propylene, ammonia and oxygen or a gas containing molecular oxygen is contacted in the presence of a catalyst, in a fixed or fluidized bed, at a temperature between 300° C and 550° C, said catalyst consisting essentially of a catalytic mixture of oxygen containing compounds represented by the empirical formula:

$$U_a Te_b Mo_c Me_d O_e$$

wherein U is uranium, Te is tellurium, Mo is molybdenum, Me is an activator element selected from the group consisting of phosphorus, arsenic, antimony and boron, O is oxygen and wherein, for $a$ equal to 1, $b$ is from 1 to 8, $c$ is from 0.1 to 0.5, $d$ is 0 to 5, and $e$ is a number taken to satisfy the oxidation state of the elements in said catalyst.

2. A process for the manufacture of acrylonitrile characterized in that a mixture of propylene, ammonia and oxygen or a gas containing molecular oxygen is contacted in the presence of a catalyst, in a fixed or fluidized bed, at a temperature between 300° C and 550° C, said catalyst consisting essentially of a catalytic mixture of oxygen containing compounds represented by the empirical formula:

$$U_a Te_b Mo_c Me_d O_e$$

wherein U is uranium, Te is tellurium, Mo is molybdenum, Me is an activator element selected from the group consisting of phosphorus, arsenic, antimony and boron, O is oxygen and wherein, for $a$ equal to 1, $b$ is from 1 to 8, $c$ is from 0.3 to 0.8, $d$ is 0 to 5, and $e$ is a number taken to satisfy the oxidation state of the elements in said catalyst.

3. A process for the manufacture of acrylonitrile characterized in that a mixture of propylene, ammonia and oxygen or a gas containing molecular oxygen is contacted in the presence of a catalyst, in a fixed or fluidized bed, at a temperature between 300° C and 550° C, said catalyst consisting essentially of a catalytic mixture of oxygen containing compounds represented by the empirical formula:

$$U_a Te_b Mo_c O_e$$

wherein U is uranium, Te is tellurium, Mo is molybdenum,
O is oxygen and wherein $a$ equals 2, $b$ is 8, $c$ is 1 and $e$ is a number taken to satisfy the oxidation state of the elements in said catalyst.

4. A process for the manufacture of acrylonitrile characterized in that a mixture of propylene, ammonia and oxygen or a gas containing molecular oxygen is contacted in the presence of a catalyst, in a fixed or fluidized bed, at a temperature between 300° C and 550° C, said catalyst consisting essentially of a catalytic mixture of oxygen containing compounds represented by the empirical formula:

$$U_a Te_b Mo_c O_e$$

wherein U is uranium, Te is tellurium, Mo is molybdenum,
O is oxygen and wherein $a$ equals 1, $b$ is 2, $c$ is 0.5 and $e$ is a number taken to satisfy the oxidation state of the elements in said catalyst.